US011744608B2

(12) United States Patent  
Neuharth et al.

(10) Patent No.: US 11,744,608 B2  
(45) Date of Patent: Sep. 5, 2023

(54) ATHERECTOMY SYSTEM WITH ELECTROMAGNETIC GUIDEWIRE CLAMP

(71) Applicant: BOSTON SCIENTIFIC SCIMED, INC., Maple Grove, MN (US)

(72) Inventors: Jarrod Kenneth Neuharth, Brooklyn Center, MN (US); Corydon Carlson, Stillwater, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 422 days.

(21) Appl. No.: 17/016,173

(22) Filed: Sep. 9, 2020

(65) Prior Publication Data

US 2021/0077143 A1     Mar. 18, 2021

Related U.S. Application Data

(60) Provisional application No. 62/899,623, filed on Sep. 12, 2019.

(51) Int. Cl.
*A61B 17/3207* (2006.01)
*A61B 17/00* (2006.01)

(52) U.S. Cl.
CPC .......... *A61B 17/320758* (2013.01); *A61B 2017/0042* (2013.01); *A61B 2017/00199* (2013.01);

(Continued)

(58) Field of Classification Search
CPC .... A61B 17/320783; A61B 17/320725; A61B 2017/320791; A61B 2017/00017; A61B 2017/22038; A61B 2017/22094; A61B 2017/00685; A61B 2017/320775; A61B 2017/003; A61B 17/320758; A61B 2017/00199; A61B 2017/00398; A61B 2017/0042; A61B 2017/00876; A61B 2017/22049; A61M 2025/09125

See application file for complete search history.

(56) References Cited

U.S. PATENT DOCUMENTS 5,318,576 A    6/1994  Plassche et al.
5,779,722 A    7/1998  Shturman et al.
(Continued)

FOREIGN PATENT DOCUMENTS

CA     2953631 A1 *  7/2018
CN    101209209 A  * 12/2006
(Continued)

OTHER PUBLICATIONS

International Search Report and Written Opinion dated Dec. 8, 2020 for International Application No. PCT/US2020/049999, pp. 1-14.

*Primary Examiner* — Kelly J Bekker
*Assistant Examiner* — Nasheha Baset
(74) *Attorney, Agent, or Firm* — Seager, Tufte & Wickhem LLP

(57) ABSTRACT

An atherectomy system includes an atherectomy burr and a drive mechanism that is adapted to rotatably actuate the atherectomy burr and to accommodate a guidewire extending therethrough. A controller is adapted to regulate operation of the drive mechanism. A guidewire extends through the drive mechanism and an electromagnetic guidewire clamp is adapted to releasably secure the guidewire relative to the drive mechanism.

19 Claims, 11 Drawing Sheets

(52) U.S. Cl.
CPC .............. *A61B 2017/00398* (2013.01); *A61B 2017/00876* (2013.01)

(56) References Cited

U.S. PATENT DOCUMENTS

| | | | |
|---|---|---|---|
| 6,149,663 A | 11/2000 | Strandberg et al. | |
| 6,503,227 B1 | 1/2003 | Guo et al. | |
| 2007/0270688 A1* | 11/2007 | Gelbart ................ | A61B 5/0538 600/427 |
| 2007/0293719 A1 | 12/2007 | Scopton et al. | |

FOREIGN PATENT DOCUMENTS

| | | | | |
|---|---|---|---|---|
| CN | 207980153 U | | 10/2018 | |
| JP | 2004514463 A | | 5/2004 | |
| KR | 20100086103 A | * | 1/2009 | |
| WO | 2001076680 A1 | | 10/2001 | |
| WO | WO-0203868 A2 | * | 1/2002 | ......... A61B 17/7041 |

* cited by examiner

ATHERECTOMY SYSTEM WITH ELECTROMAGNETIC GUIDEWIRE CLAMP

CROSS-REFERENCE TO RELATED APPLICATIONS

This application claims the benefit of priority under 35 U.S.C. § 119 to U.S. Provisional Application Ser. No. 62/899,623, filed Sep. 12, 2019, the entirety of which is incorporated herein by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, an atherectomy system includes an atherectomy burr and a drive mechanism that is adapted to rotatably actuate the atherectomy burr. The drive mechanism is adapted to accommodate a guidewire extending therethrough. A controller is adapted to regulate operation of the drive mechanism. A guidewire extends through the drive mechanism and an electromagnetic guidewire clamp is adapted to releasably secure the guidewire relative to the drive mechanism.

Alternatively or additionally, the electromagnetic guidewire clamp may include a clamp housing, an electromagnet secured within the clamp housing and a steel plunger that is slidingly disposed within the clamp housing such that the steel plunger can move towards the electromagnet when the electromagnet is actuated and can move away from the electromagnet when the electromagnet is not actuated. Actuating the electromagnet causes the steel plunger to move towards the electromagnet, thereby clamping the guidewire between the electromagnet and the steel plunger.

Alternatively or additionally, the electromagnetic guidewire clamp may further include a guidewire lead-in that is molded into the clamp housing to facilitate advancing the guidewire through the electromagnetic guidewire clamp.

Alternatively or additionally, the electromagnetic guidewire clamp may further include a first resilient pad that is secured to a side of the electromagnet facing the steel plunger and a second resilient pad that is secured to a side of the steel plunger facing the electromagnet.

Alternatively or additionally, the clamp housing may include a lower clamp housing that is adapted to accommodate the steel plunger therein and an upper clamp housing that is adapted to accommodate the electromagnet therein.

Alternatively or additionally, the clamp housing may further include a cap secured relative to the upper clamp housing.

Alternatively or additionally, the electromagnet may be secured relative to the upper clamp housing via a mounting fastener that extends through the cap and into the electromagnet.

Alternatively or additionally, the drive mechanism may include a drive cable that is coupled with the atherectomy burr and a drive motor that is adapted to rotate the drive cable.

Alternatively or additionally, the atherectomy system may further include a handle including a handle housing, the drive motor disposed within the handle housing.

Alternatively or additionally, the electromagnetic guidewire clamp may be disposed within the handle housing.

Another example is an atherectomy system that includes a handle including a handle housing and an atherectomy burr. A drive motor is disposed within the handle housing and is adapted to rotatably actuate the atherectomy burr via a drive cable extending from the drive motor to the atherectomy burr, the drive cable adapted to accommodate a guidewire extending through the drive cable. A controller is adapted to regulate operation of the drive mechanism. An electromagnetic guidewire clamp is adapted to releasably secure the guidewire relative to the drive cable and includes an electromagnet and a steel plunger that is slidingly disposed relative to the electromagnetic such that the steel plunger can move towards the electromagnet when the electromagnet is actuated and clamp the guidewire between the electromagnet and the steel plunger.

Alternatively or additionally, the electromagnet may be secured relative to the handle housing.

Alternatively or additionally, the steel plunger may be slidingly secured relative to the handle housing.

Alternatively or additionally, the atherectomy system may further include an electromagnetic guidewire clamp housing that is secured within the handle housing.

Alternatively or additionally, the electromagnetic guidewire clamp housing may include a lower clamp housing that may be adapted to accommodate the steel plunger therein and an upper clamp housing that may be adapted to accommodate the electromagnet therein.

Alternatively or additionally, the electromagnetic guidewire clamp housing may further include a cap secured relative to the upper clamp housing.

Alternatively or additionally, the electromagnet may be secured relative to the upper clamp housing via a mounting fastener that extends through the cap and into the electromagnet.

Alternatively or additionally, the electromagnetic guidewire clamp may further include a first resilient pad that is secured to a side of the electromagnet facing the steel plunger and a second resilient pad secured to a side of the steel plunger facing the electromagnet.

Another example is an atherectomy system including an atherectomy burr and a drive mechanism that is adapted to rotatably actuate the atherectomy burr, the drive mechanism adapted to accommodate a guidewire extending therethrough. A controller is adapted to regulate operation of the drive mechanism. A guidewire extends through the drive mechanism and an electrically actuated guidewire clamp is adapted to releasably secure the guidewire relative to the drive mechanism.

Alternatively or additionally, the electrically actuated guidewire clamp may include an electromagnet and a steel plunger slidingly disposed relative to the electromagnetic such that the steel plunger can move towards the electromagnet when the electromagnet is actuated and clamp the guidewire between the electromagnet and the steel plunger.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
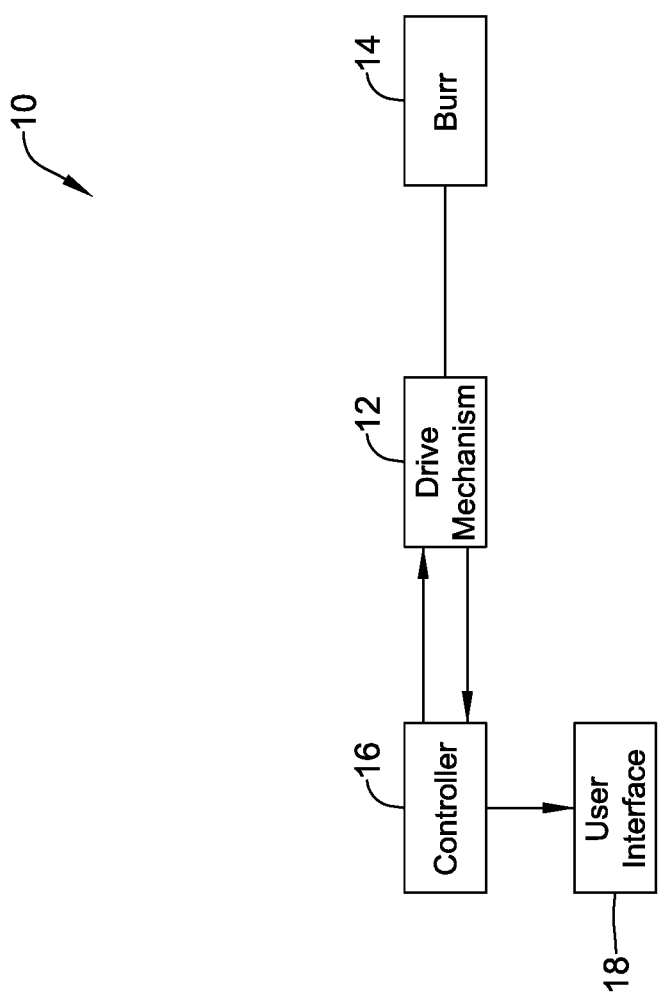
FIG. 1 is a schematic block diagram of an example atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

FIG. 1 is a schematic block diagram of an example atherectomy system 10 that includes a drive mechanism 12 that is adapted to rotatably actuate an atherectomy burr 14. The atherectomy system 10 includes a controller 16 that is adapted to regulate operation of the drive mechanism 12. In some cases, the atherectomy system 10 may include a user interface 18 that may be operably coupled to the controller 16 such that the controller 16 is able to display information regarding the performance of the drive mechanism 12. This information may, for example, include one or more of an instantaneous speed of the drive mechanism 12, an instantaneous torque being experienced by the atherectomy burr 14, and the like. In some instances, the atherectomy system 10 may not include the user interface 18. In some cases, the atherectomy burr 14 may also be referred to as being or including a cutting head or a cutting member, and these terms may be used interchangeably.

Figure 2:
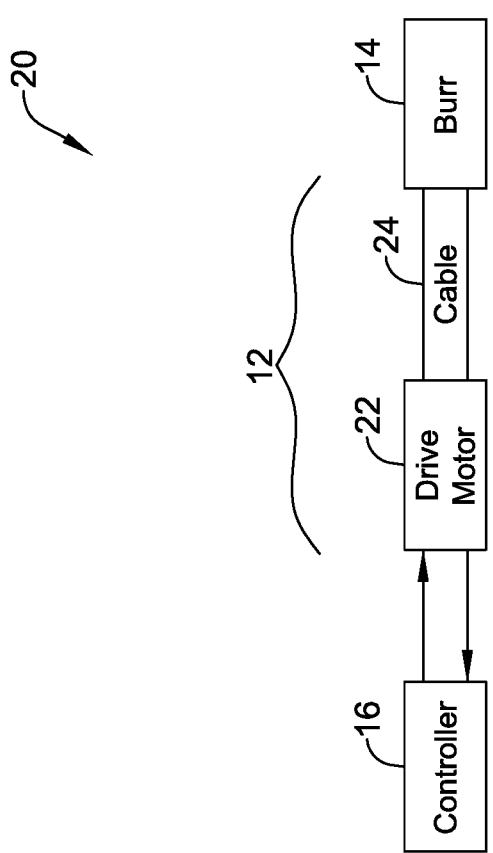
FIG. 2 is a schematic block diagram of an example atherectomy system.

FIG. 2 is a schematic block diagram of an example atherectomy system 20 in which the drive mechanism 12 may include a drive motor 22 and a drive cable 24 that is operably coupled with the drive motor 22 as well as the atherectomy burr 14. In some cases, features of the atherectomy system 20 may be combined with features of the atherectomy system 10. In some cases, the atherectomy system 20 may also include a handle (not shown).

Figure 3:
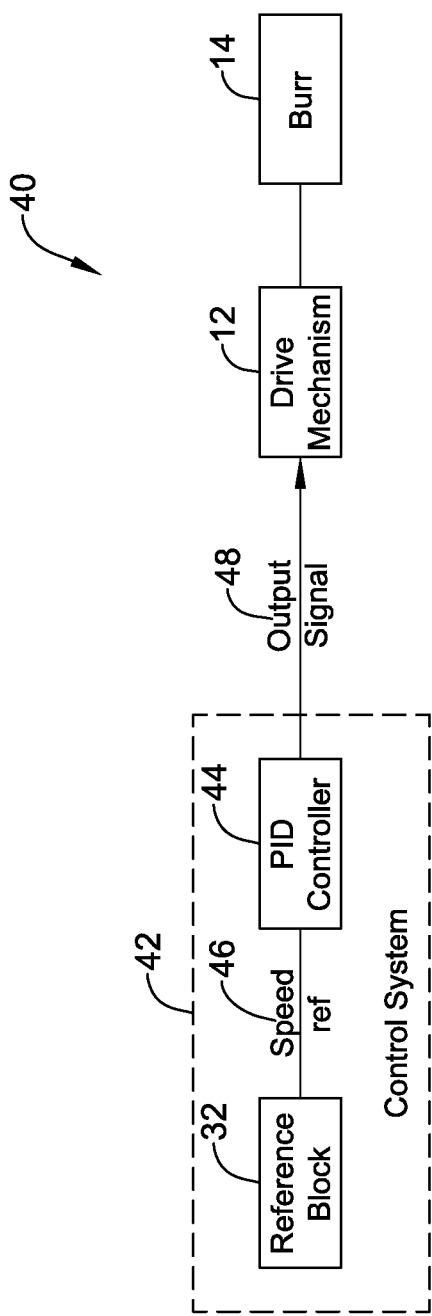
FIG. 3 is a schematic block diagram of an example atherectomy system.

FIG. 3 is a schematic block diagram of an example atherectomy system 40 that includes a control system 42 that is adapted to regulate operation of the drive mechanism 12 in order to rotatably actuate the atherectomy burr 14. In some cases, features of the atherectomy system 40 may be combined with one or more of the atherectomy system 10 and the atherectomy system 20. The control system 42 may include a reference block 32 as well as a Proportional Integral Derivative (PID) controller 44 that is operably coupled to the reference block 32. In some cases, the reference block 32 may determine a speed reference 46 that is selectable between a nominal value, a negative value and zero. In some instances, the PID controller 44 may be further adapted to add an offset value to the speed reference 46 received from the reference block 32, thereby outputting an Output Signal 48, although in some cases, the reference block 32 may add the offset value. The PID controller 44 may be further adapted to provide a reduction in motor speed of the drive mechanism 12 that is greater than what would otherwise normally occur in response to an increasing torque experienced at the atherectomy burr 14.

Figure 4:
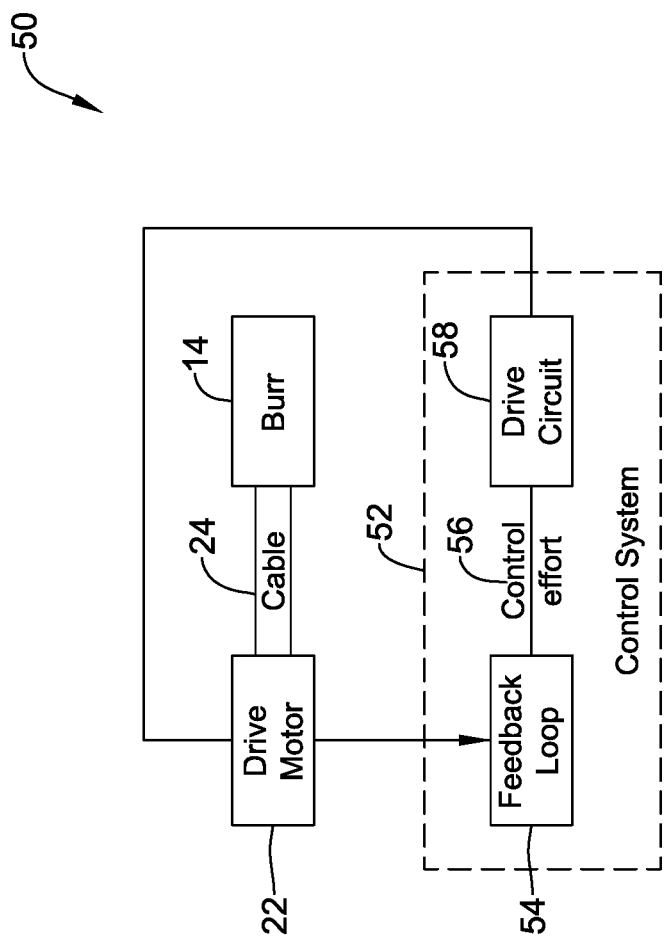
FIG. 4 is a schematic block diagram of an example atherectomy system.

FIG. 4 is a schematic block diagram of an example atherectomy system 50 that includes a control system 52 that is adapted to regulate operation of the drive motor 22 in order to rotatably actuate the atherectomy burr 14. In some cases, features of the atherectomy system 50 may be combined with one or more of the atherectomy system 10, the atherectomy system 20 or the atherectomy system 40. The control system 52 is operably coupled to the drive motor 22 and includes a feedback loop 54 that is adapted to monitor performance of the drive motor 22 and to output a control effort signal 56. A drive circuit 58 is adapted to receive the control effort signal 56 and to regulate operation of the drive motor 22 in accordance with the control effort signal 56.

In some cases, the feedback loop 54 may include a reference block for determining a speed reference and a Proportional Integral Derivative (PID) controller that is operably coupled to the reference block for receiving the speed reference, the PID controller adapted to utilize the speed reference, a Proportional (P) gain value, an Integral (I) gain value and a Derivative (D) gain value in determining the control effort signal. In some cases, the feedback loop 54 may be adapted to add an offset value to a reference signal provided to the reference loop 54 in order to accurately hold speed of the drive motor 22 during a no-load situation. In some instances, for example if the atherectomy burr 14 becomes stuck, the control system 52 may be further adapted to increase the torque provided by the drive motor 22 until a torque threshold is reached for a brief period of time, and to subsequently direct the drive motor 22 to reverse at a slow speed in order to unwind energy in the drive mechanism.

Figure 5:
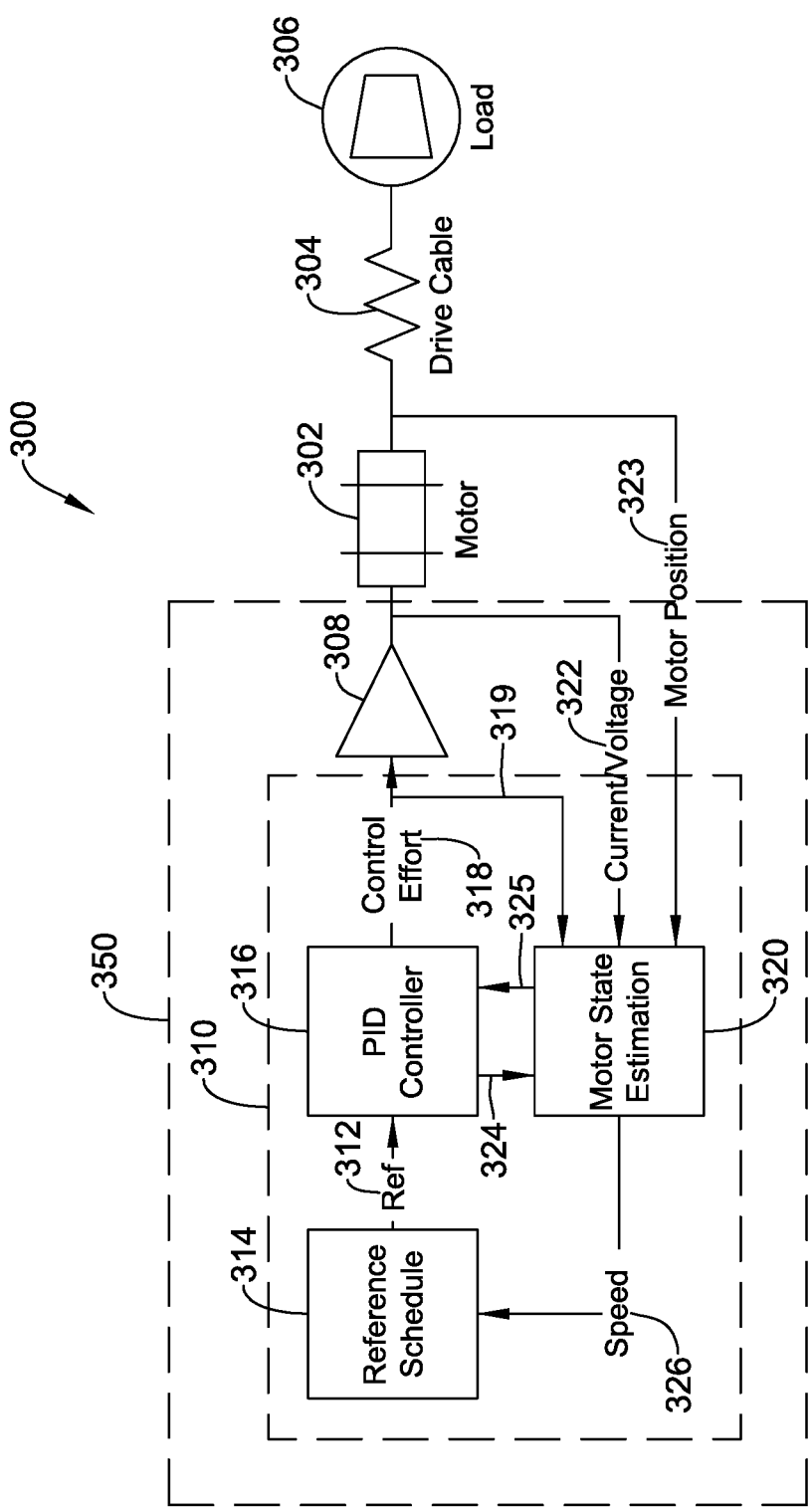
FIG. 5 is a schematic block diagram of an example atherectomy system.

FIG. 5 is a schematic block diagram of an example atherectomy system 300. In some cases, the atherectomy system 300 may be considered as being an example of the atherectomy system 10, 20, 40 or 50. In some instances, features of the atherectomy system 300 may be combined with features of any of the atherectomy systems 10, 20, 40 or 50, for example. The atherectomy system 300 includes a motor 302 that drives a drive cable 304 which itself engages a load 306. The load 306 represents an atherectomy burr, for example. The motor 302 is controlled by a drive circuitry 308 which may be considered as being an example of or otherwise incorporated into the drive motor 22 (FIG. 2) and/or the controller 16 (FIGS. 1 and 2), for example. In some cases, the motor 302 may be sized, relative to the weight and other dimensions of the atherectomy system 300, to be capable of accelerating the atherectomy burr to full speed in less than 3 seconds, or in some cases in less than 2 seconds. As an example, the motor 302 may be rated for at least 60 watts. In a particular example, the motor 302 may be rated for about 80 watts. These are just examples.

The drive circuitry 308 receives an input from a feedback portion 310. In some cases, the feedback portion 310 begins with a reference input 312 from a reference schedule block 314, which provides the reference input 312 to a PID controller 316. In some cases, the reference schedule block 314 may be configured to accept additional inputs, such as from a user and/or from additional sensors not illustrated. As an example, if the device has been running for too long of a period of time, the reference schedule block 314 may reduce the speed reference in order to prevent overheating. A PID controller is a controller that includes a (P) proportional portion, an (I) integral portion and a (D) derivative portion. The PID controller 316 outputs a control effort value or reference current 318 to the drive circuitry 308. A motor state estimation block 320 receives a current/voltage signal 322 and a motor position signal 323 from the drive circuitry 308 and receives state feedback 324 from the PID controller 316. The motor state estimation block 320 provides a state feedback signal 325 back to the PID controller 316.

The motor state estimation block 320 outputs a speed value 326 back to the reference schedule block 314. While the feedback from the motor state estimation block 320 to the reference schedule block 314 is shown as being a speed value, in some cases the feedback may additionally or alternatively include one or more of position, torque, voltage or current, and in some cases may include the derivative or integral of any of these values. In some cases, the motor state estimation block 320 may instead receive a signal 323 that represents speed, instead of position (as illustrated). The motor position signal 323 may be an indication of relative rotational position of an output shaft of the motor 302, and thus an indication of relative rotational position of the load 306, which if tracked over time may provide an indication of speed.

In some cases, the drive circuitry 308 and the feedback loop 310 may in combination be considered as forming a controller 350 that is adapted to determine an estimated torque at the atherectomy burr (the load 306 as shown in FIG. 5). The controller 350 may be considered as being an example of the controller 16 (FIG. 1). In some cases, the controller 350 may be considered as including only some elements of the drive circuitry 308 and the feedback loop 310. In some instances, some of the features and functions of the controller 350 may take place in the motor state estimation block 320. It will be appreciated that while FIG. 5 shows various components as standalone components, in some cases the functions of one or more of the components may actually be spread between separate components. In some instances, the functions of one or more of the components may be combined into one or more components.

If the estimated torque at the load 306 becomes too high, this may be an indication that the burr is getting stuck. In order to protect against possible damage to the drive cable 304, and to protect against possible injury to the patient, the atherectomy system 300 may be adapted to stop or even reverse operation of the atherectomy system 300 if the estimated torque meets or exceeds a predetermined torque threshold. It will be appreciated that the actual value of the predetermined torque threshold may vary, depending on the mechanics of the atherectomy system 300, but may be set at a level low enough to prevent damage and injury, but not set so low as to engender too many false alarms caused by minor and/or temporary torque increases that are not caused by the load 306 becoming stuck. For example, the instantaneous torque may vary by small amounts as the atherectomy system 300 progresses through the patient's vasculature.

Figure 6:
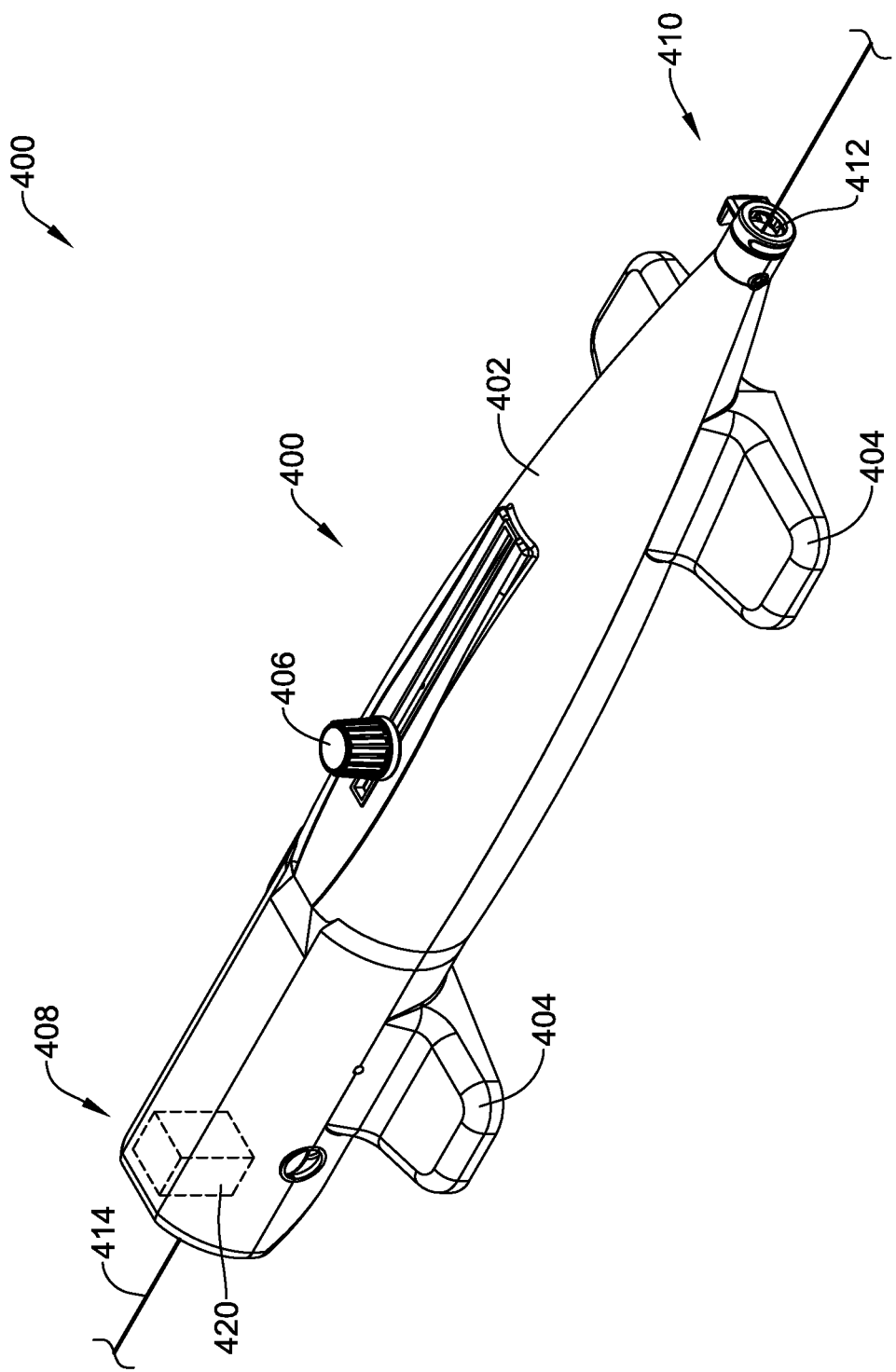
FIG. 6 is a perspective view of an example atherectomy system.

FIG. 6 is a perspective view of an example atherectomy system 400. In some cases, the atherectomy system 400 may be considered as being a manifestation of the atherectomy system 10, 20, 40, 50 or 300. In some instances, features of the atherectomy system 400 may be combined with features of any of the atherectomy systems 10, 20, 40, 50 or 300, for example. The atherectomy system 400 includes a handle 402. While not illustrated, it will be appreciated that the atherectomy system 400 includes a drive mechanism (such as the drive mechanism 12 shown in FIGS. 1-3) and a controller (such as the controller 16 shown in FIGS. 1-2) that is disposed within the handle 402 and that regulates operation of the drive mechanism. The handle 402 may, for example, include feet 404 that serve to stabilize the handle 402 on a flat surface during operation. A control mechanism 406 extends out of the handle 402 and may be used in controlling one or more features of the atherectomy system 400 during use. For example, the control mechanism 406 may be used to allow a user to change an operating speed of the drive mechanism.

The handle 402 includes a proximal region 408 and a distal region 410. As can be seen, the distal region 410 includes an aperture 412 that is adapted to permit a drive cable (such as the drive cable 24 of FIGS. 2 and 4 or the drive cable 304 of FIG. 5) to exit the handle 402. While not visible, the proximal region 408 may be configured to accommodate a guidewire 414 extending through the atherectomy system 400. It will be appreciated that at the distal region 410, the guidewire 414 will extend through the drive cable that is not shown in this illustration.

The atherectomy system 400 includes an electrically actuated guidewire clamp 420, which is schematically shown in phantom block diagram in FIG. 6. It will be appreciated that in some cases, a guidewire clamp may be referred to as a guide wire brake. In some cases, the guidewire clamp 420 may be an electromagnetic guidewire clamp. The electromagnetic guidewire clamp 420 may be disposed within an interior of the handle 402 and may be configured to reversibly clamp down onto the guidewire 414 in order to prevent movement of the guidewire 414 during operation of the atherectomy system 400. The electromagnetic guidewire clamp 420 may be configured to permit the guidewire 414 to move axially relative to the handle 402 in order to advance the atherectomy system 400 over the guidewire 414. The electromagnetic guidewire clamp 420 may be considered, therefore, as having a clamped configuration and an unclamped configuration. Put another way, the electromagnetic guidewire clamp 420 may be considered as being able to be actuated from the unclamped configuration to the clamped configuration.

In some cases, the controller 350 (FIG. 5) may be configured to automatically actuate the electromagnetic guidewire clamp 420 before allowing the drive motor 22, 302 to operate. The controller 350 may automatically and immediately stop operation of the drive motor 22, 302 if any predetermined values or thresholds are detected with the electromagnetic guidewire clamp 420.

Figure 7:
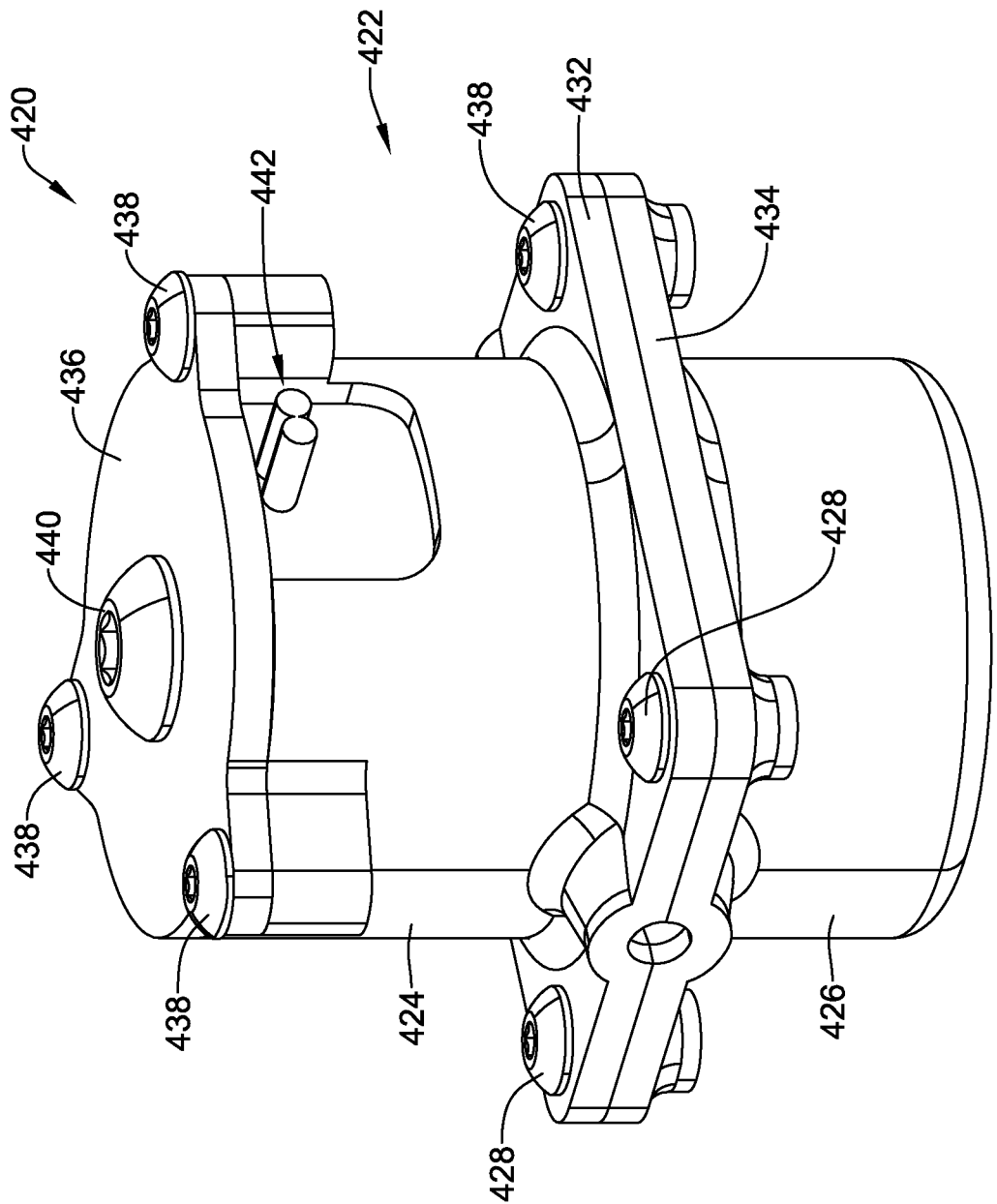
FIG. 7 is a perspective view of an example electromagnetic guidewire clamp usable in the example atherectomy system of FIG. 6.
Figure 8:
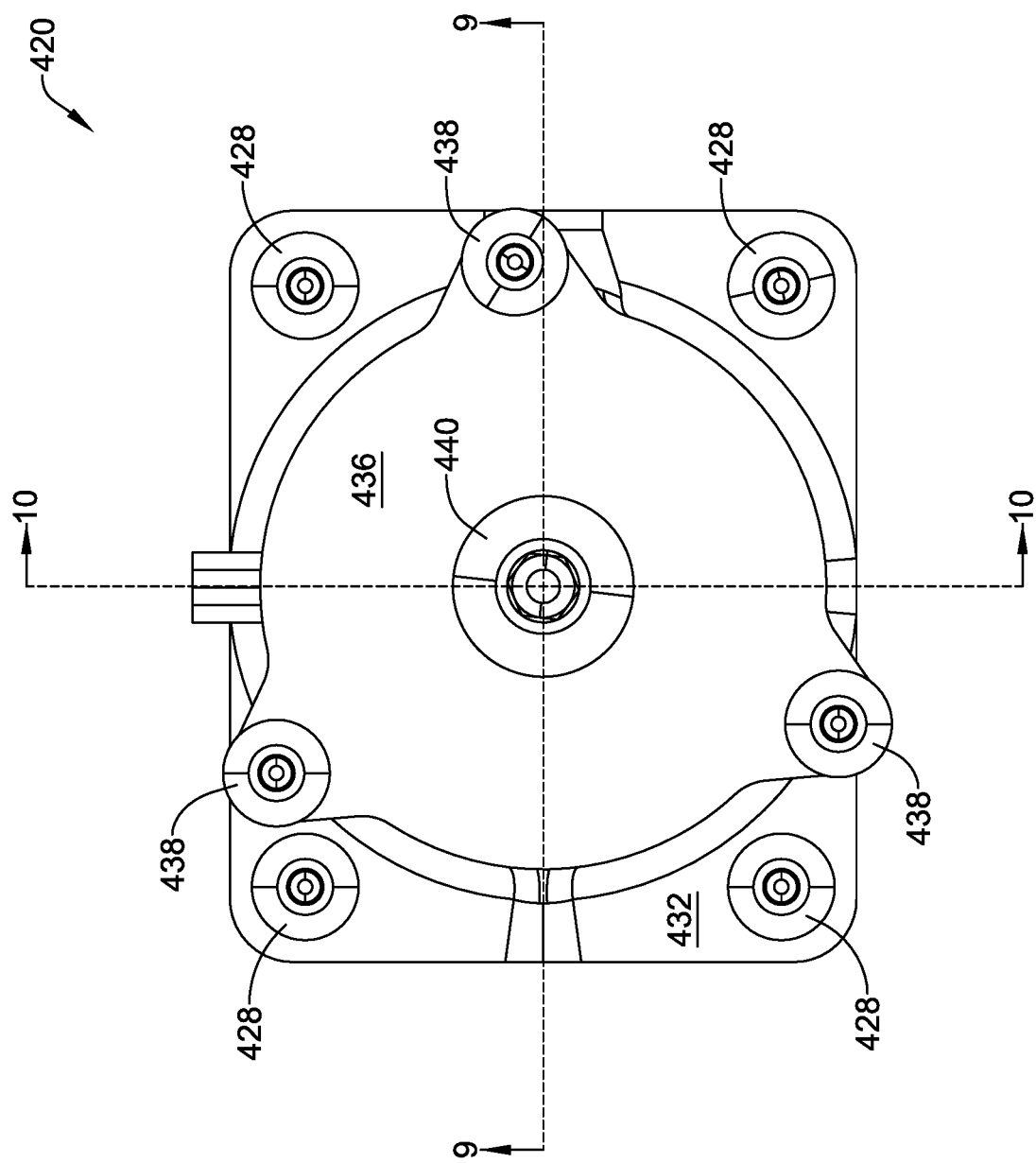
FIG. 8 is a top view of the example electromagnetic guidewire clamp of FIG. 7.

FIG. 7 is a perspective view of an example of the electromagnetic guidewire clamp 420. FIG. 8 is a top view of the electromagnetic guidewire clamp 420, illustrating how several cross-sections may be taken. The electromagnetic guidewire clamp 420 includes a clamp housing 422. In some cases, the clamp housing, or guidewire clamp housing, 422 may be considered as including an upper clamp housing 424 and a lower clamp housing 426. As illustrated, the upper clamp housing 424 and the lower clamp housing 426 are shown as being fastened together via fasteners 428 that extend between an upper clamp housing flange 432 and a lower clamp housing flange 434. In some cases, the fasteners 428 may be screws, bolts, or rivets. In some cases, the upper clamp housing flange 432 and the lower clamp housing flange 434 may be adhesively secured together. These are just examples. The clamp housing 422 also includes a cap 436. The cap 436 may be secured to the upper clamp housing 424 via fasteners 438. As can be seen, a fastener 440 extends down into the cap 436. As will be discussed relative to FIG. 9, the fastener 440 may be used to secure an internal component of the electromagnetic guidewire clamp 420. Also shown in FIG. 7 is a pair of electrical conductors 442 that are operably coupled to the aforementioned internal component.

Figure 9:
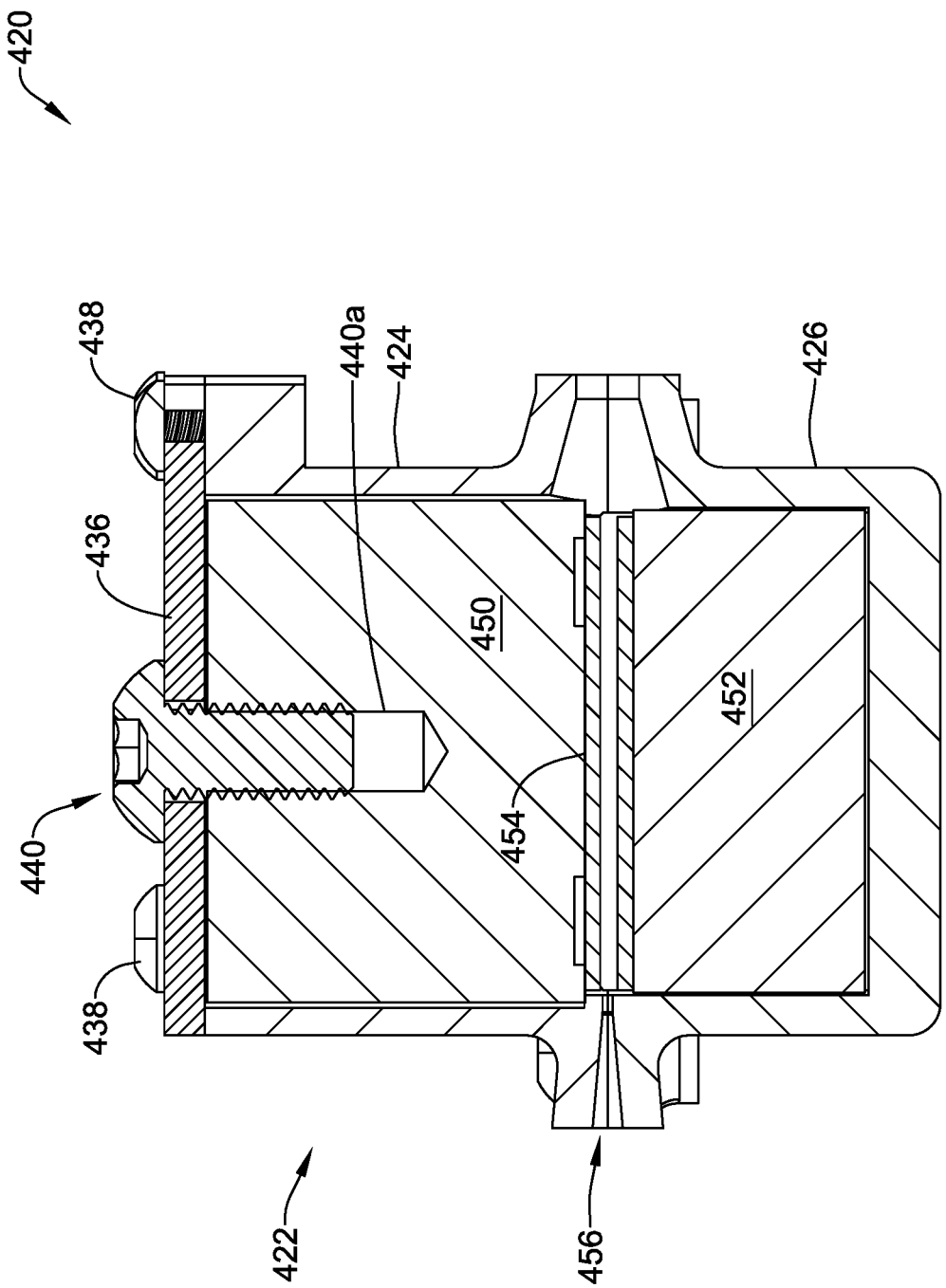
FIG. 9 is a cross-sectional view of the example electromagnetic guidewire clamp, taken along the line 9-9 of FIG. 8.

FIG. 9 is a cross-sectional view of the electromagnetic guidewire clamp 420, taken along the line 9-9 of FIG. 8. The electromagnetic guidewire clamp 420 includes an electromagnet 450 and a steel plunger 452. The electromagnet 450 may be considered as being secured relative to the upper clamp housing 424 via interaction between the fastener 442 and a corresponding threaded aperture 442a that is formed within the electromagnet 450. The steel plunger 452 may be considered as being slidingly disposed relative to the lower clamp housing 426. In an un-actuated configuration, in which the electromagnet 450 is not electrically energized, there is a gap 454 between the electromagnet 450 and the steel plunger 452 that accommodates passage of the guidewire 414 (FIG. 6). The upper clamp housing 424 and the lower clamp housing 426 cooperate to form a guidewire lead-in 456. The guidewire lead-in 456 may be internally tapered, to make it easier to extend the guidewire 414 into the electromagnetic guidewire clamp 420.

Figure 10:
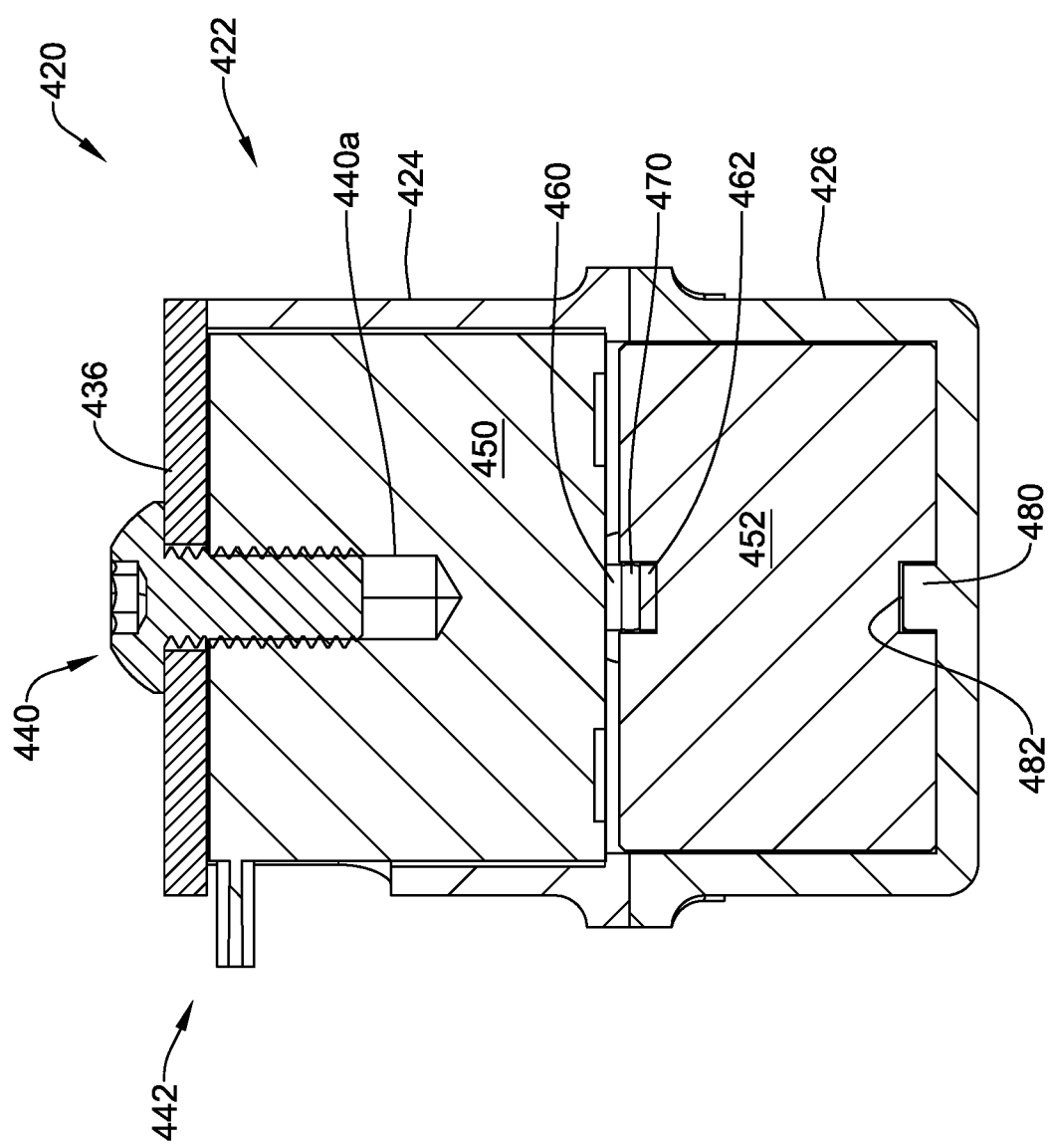
FIG. 10 is a cross-sectional view of the example electromagnetic guidewire clamp, taken along the line 10-10 of FIG. 8 with the electromagnetic guidewire clamp shown in an unclamped configuration.

FIG. 10 is a cross-sectional view of the electromagnetic guidewire clamp 420, taken along the line 10-10 of FIG. 8. In some cases, the electromagnetic guidewire clamp 420 may include a first resilient pad 460 that is secured to a side of the electromagnet 450 facing the steel plunger 452 and a second resilient pad 462 that is secured to a side of the steel plunger 452 facing the electromagnet 450. It will be appreciated that the first resilient pad 460 and the second resilient pad 462 may, in combination, help to secure the guidewire 414 from relative movement when the electromagnet 450 is actuated and the steel plunger 452 moves upward (in the illustrated orientation) towards the electromagnet 450. The first and second resilient pads 460, 462 may be made of any suitable electrically insulating (non-conducting) material, such as but not limited to silicone, Neoprene, Nitrile, EPFM and others.

It will be appreciated that the view in FIG. 10 is rotated 90 degrees from that shown in FIG. 9. In this view, it can be seen that the steel plunger 452 includes a recess 470 that extends across a top of the steel plunger 452. In this view, it can be seen that the first resilient pad 460 is a relatively narrow strip and the second resilient pad 462 is also a relatively narrow strip. Moreover, the second resilient pad 462 can be seen as being disposed within the recess 470 and the first resilient pad 460 is secured relative to the electromagnet 450 and aligned with the recess 470 and with the second resilient pad 462. In some cases, as illustrated, the lower clamp housing 424 may define an alignment peg 480 that aligns with a corresponding alignment aperture 482 that is formed within the steel plunger 452. The alignment peg 480 and the alignment aperture 482 may cooperate to limit relative radial movement of the steel plunger 452 relative to the lower clamp housing 424. In some cases, it is contemplated that the alignment aperture 482 is sized the same as the recess 470 such that the steel plunger 452 may be installed in either of two vertical positions that are 180 degrees apart.

Figure 11:
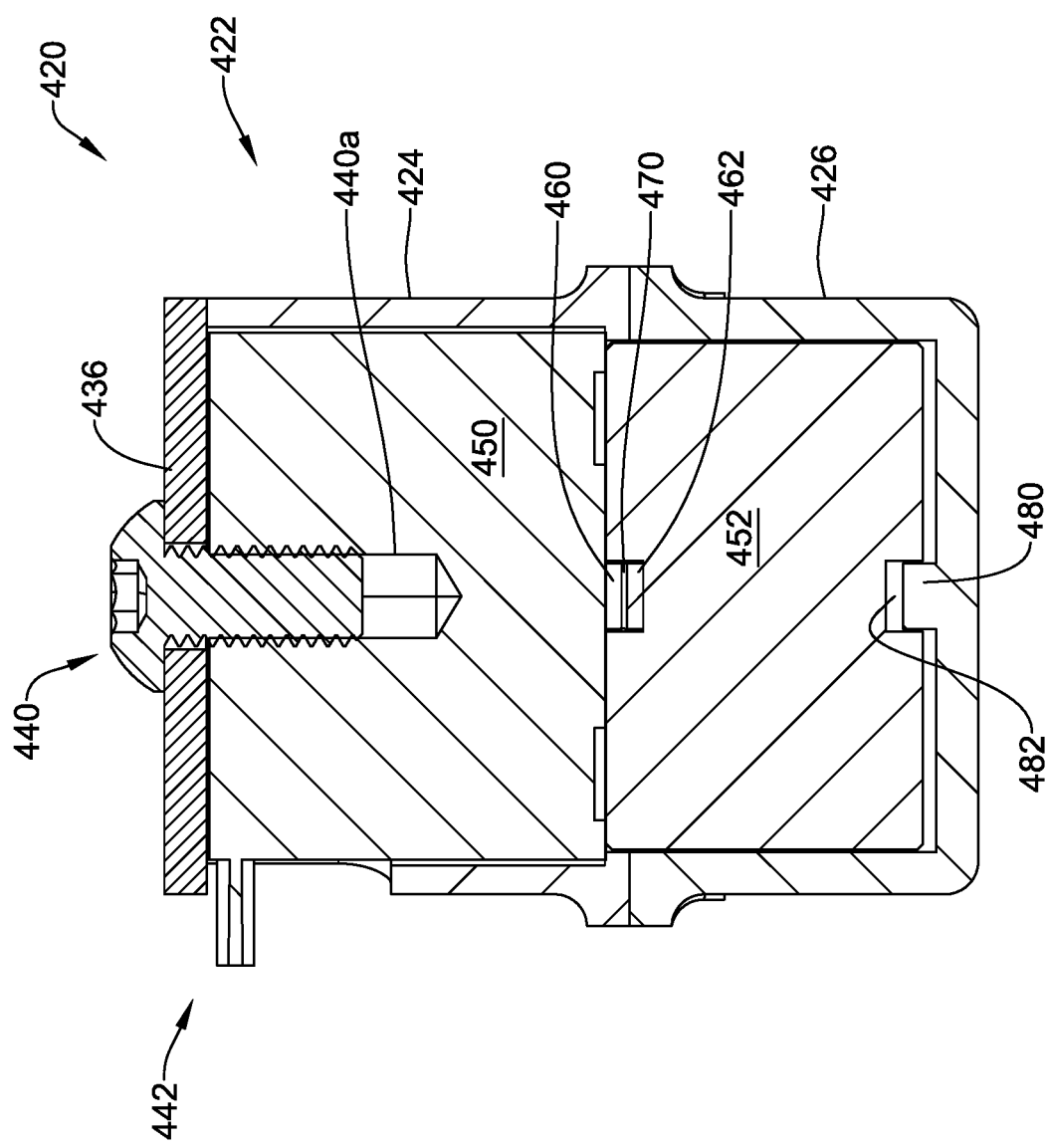
FIG. 11 is a schematic cross-sectional view of the example electromagnetic guidewire clamp, taken along the line 10-10 of FIG. 8 with the electromagnetic guidewire clamp shown in a clamped configuration.

FIG. 10 shows the electromagnetic guidewire clamp 420 in an un-clamped position in which the electromagnet 450 is not electrically actuated while FIG. 11 shows the electromagnetic guidewire clamp 420 in a clamped position in which the electromagnet 450 has been electrically actuated. As can be seen by comparing FIG. 11 to FIG. 10, the steel plunger 452 has moved upward (in the illustrated orientation) towards the electromagnet 450. It can be seen that the first resilient pad 460 and the second resilient pad 462 together substantially fill the recess 470, thereby clamping the guidewire 414 (not shown in FIG. 11) therebetween. Similarly, a space is now visible between the alignment peg 480 and the corresponding alignment aperture 482 at the bottom of the steel plunger 452, indicating that the steel plunger 452 has moved relative to the lower clamp housing 424.

As described herein, the electromagnetic guidewire clamp 420 may be considered as being biased by gravity into the un-clamped configuration illustrated in FIG. 10. Providing an electrical current to the electromagnet 450 causes the steel plunger 452 to move closer to the electromagnet 450 and thus into the clamped configuration illustrated in FIG. 11. Removing the electrical current will allow the electromagnetic guidewire clamp 420 to revert to the un-clamped configuration.

Other ways of forming a guidewire clamp are contemplated. For example, the guidewire clamp may include two electromagnets, or one magnet and one electromagnet, that are mechanically biased towards each other, such as but not limited to using one or more springs to provide the mechanical bias. Thus, the guidewire clamp would be biased into the clamped configuration. In order to move the two magnets away from each other, currents may be selectively applied to both electromagnets (or to the single electromagnet) such that the magnets repel each other, thereby moving into an un-clamped configuration so that a guidewire may be extended through. Shutting off the current would cause the magnets to once again move towards each other to hold the guidewire in place. In some cases, both magnets may be free to move, while in other cases one magnet would be fixed in place and the other would be free to move. It will be appreciated that such a guidewire clamp, with two electromagnets or one electromagnet and one magnet may include housing elements that facilitate relative movement between the two electromagnets or the electromagnet and the magnet. These are just examples.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy system, comprising:
    an atherectomy burr;
    a drive mechanism adapted to rotatably actuate the atherectomy burr, the drive mechanism adapted to accommodate a guidewire extending therethrough;
    a controller adapted to regulate operation of the drive mechanism;
    a guidewire extending through the drive mechanism; and
    an electromagnetic guidewire clamp adapted to releasably secure the guidewire relative to the drive mechanism, the electromagnetic guidewire clamp comprising:
        a primary clamp housing;
        an electromagnet secured within the primary clamp housing;
        a plunger slidingly disposed within the primary clamp housing such that the plunger can move towards the electromagnet when the electromagnet is actuated and can move away from the electromagnet when the electromagnet is not actuated;
        wherein actuating the electromagnet causes the plunger to move towards the electromagnet, thereby clamping the guidewire between the electromagnet and the plunger.

2. The atherectomy system of claim 1, wherein the plunger comprises a steel plunger.

3. The atherectomy system of claim 1, wherein the electromagnetic guidewire clamp further comprises:
    a guidewire lead-in molded into the primary clamp housing to facilitate advancing the guidewire through the electromagnetic guidewire clamp.

4. The atherectomy system of claim 1, wherein the electromagnetic guidewire clamp further comprises:
    a first resilient pad secured to a side of the electromagnet facing the steel plunger; and
    a second resilient pad secured to a side of the steel plunger facing the electromagnet.

5. The atherectomy system of claim 1, wherein the primary clamp housing comprises:
    a lower clamp housing adapted to accommodate the steel plunger therein; and
    an upper clamp housing adapted to accommodate the electromagnet therein.

6. The atherectomy system of claim 5, wherein the primary clamp housing further comprises a cap secured relative to the upper clamp housing.

7. The atherectomy system of claim 6, wherein the electromagnet is secured relative to the upper clamp housing via a mounting fastener that extends through the cap and into the electromagnet.

8. The atherectomy system of claim 1, wherein the drive mechanism comprises:
    a drive cable coupled with the atherectomy burr; and
    a drive motor adapted to rotate the drive cable.

9. The atherectomy system of claim 8, further comprising a handle including a handle housing, the drive motor disposed within the handle housing.

10. The atherectomy system of claim 9, wherein the electromagnetic guidewire clamp is disposed within the handle housing.

11. An atherectomy system, comprising:
a handle including a handle housing;
an atherectomy burr;
a drive motor disposed within the handle housing and adapted to rotatably actuate the atherectomy burr via a drive cable extending from the drive motor to the atherectomy burr, the drive cable adapted to accommodate a guidewire extending through the drive cable;
a controller adapted to regulate operation of the drive motor; and
an electromagnetic guidewire clamp adapted to releasably secure the guidewire relative to the drive cable, the electromagnetic guidewire clamp including:
an electromagnet; and
a steel plunger slidingly disposed relative to the electromagnetic such that the steel plunger can move towards the electromagnet when the electromagnet is actuated and clamp the guidewire between the electromagnet and the steel plunger.

12. The atherectomy system of claim 11, wherein the electromagnet is secured relative to the handle housing.

13. The atherectomy system of claim 11, wherein the steel plunger is slidingly secured relative to the handle housing.

14. The atherectomy system of claim 11, further comprising an electromagnetic guidewire clamp housing that is secured within the handle housing.

15. The atherectomy system of claim 14, wherein the electromagnetic guidewire clamp housing includes a lower clamp housing that is adapted to accommodate the steel plunger therein and an upper clamp housing that is adapted to accommodate the electromagnet therein.

16. The atherectomy system of claim 15, wherein the electromagnetic guidewire clamp housing further comprises a cap secured relative to the upper clamp housing.

17. The atherectomy system of claim 16, wherein the electromagnet is secured relative to the upper clamp housing via a mounting fastener that extends through the cap and into the electromagnet.

18. The atherectomy system of claim 11, wherein the electromagnetic guidewire clamp further comprises:
a first resilient pad secured to a side of the electromagnet facing the steel plunger; and
a second resilient pad secured to a side of the steel plunger facing the electromagnet.

19. An atherectomy system, comprising:
an atherectomy burr;
a drive mechanism adapted to rotatably actuate the atherectomy burr, the drive mechanism adapted to accommodate a guidewire extending therethrough;
a controller adapted to regulate operation of the drive mechanism;
a guidewire extending through the drive mechanism; and
an electrically actuated guidewire clamp adapted to releasably secure the guidewire relative to the drive mechanism, the electrically actuated guidewire clamp comprising an electromagnet and a steel plunger slidingly disposed relative to the electromagnet such that the steel plunger can move towards the electromagnet when the electromagnet is actuated and clamp the guidewire between the electromagnet and the steel plunger.

* * * * *